United States Patent
Cyr et al.

(10) Patent No.: US 6,534,480 B2
(45) Date of Patent: *Mar. 18, 2003

(54) COMPOSITIONS FOR INCREASING ENERGY IN VIVO

(75) Inventors: John St. Cyr, Coon Rapids, MN (US); Clarence A. Johnson, Wyoming, MN (US)

(73) Assignee: Bioenergy Inc., Ham Lake, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/740,255

(22) Filed: Dec. 18, 2000

(65) Prior Publication Data

US 2002/0072501 A1 Jun. 13, 2002

Related U.S. Application Data

(63) Continuation of application No. PCT/US99/13720, filed on Jun. 17, 1999.

(51) Int. Cl.[7] ............................................. A61K 31/70
(52) U.S. Cl. ........................................................ 514/23
(58) Field of Search .......................................... 514/23

(56) References Cited

U.S. PATENT DOCUMENTS

| | | | |
|---|---|---|---|
| 4,605,644 A | 8/1986 | Foker | 514/45 |
| 4,719,201 A | 1/1988 | Foker | 514/23 |
| 4,824,660 A | 4/1989 | Angello et al. | 424/1.1 |
| 4,871,718 A | 10/1989 | Carniglia | 514/23 |
| 4,920,098 A | 4/1990 | Cotter et al. | 514/2 |
| 4,968,719 A | 11/1990 | Brevetti | 514/556 |
| 5,114,723 A | 5/1992 | Stray-Gundersen | 426/74 |
| 5,292,538 A | 3/1994 | Paul et al. | 426/74 |
| 5,391,550 A | 2/1995 | Carniglia et al. | 514/23 |
| 5,707,971 A | 1/1998 | Fahy | 514/43 |
| 5,714,515 A | 2/1998 | Bunger | 514/557 |

FOREIGN PATENT DOCUMENTS

| | | | | |
|---|---|---|---|---|
| DE | 4228215 A1 | 3/1994 | | A61K/31/70 |
| EP | 0312249 | 4/1989 | | A61K/33/08 |
| EP | 0573466 | 12/1993 | | A61K/31/70 |
| EP | 0680945 | 11/1995 | | C07C/229/22 |
| WO | 94/02127 | 2/1994 | | A61K/31/195 |
| WO | 96/18313 | 6/1996 | | A23L/1/305 |

OTHER PUBLICATIONS

Angello, D.A., et al., "Effect of ribose on thallium–201 myocardial redistribution", *The Journal of Nuclear Medicine, vol. 29, No. 12*, pp. 1943–1950, (Dec. 1988).

Angello, D.A., et al., "Recovery of Myocardial Function and Thallium 201 Redistribution Using Ribose", *American Journal of Cardiac Imaging, 3(4)*, pp. 256–265, (Dec. 1989).

Batista, R., et al., "Partial left ventriculectomy—the Batista procedure", *European Journal of Cardio–Thoracic Surgery, 15 (Suppl, 1)*, pp. S12–S19, (Jan. 1999).

Bax, J.J., et al., "Accuracy of Currently Available Techniques for Prediction of Functional Recovery After Revasularization in Patients With Left Ventricular Dysfunction Due to Chronic Coronary Artery Disease: Comparison of Pooled Data", *Journal of the American College of Cardiology, 30 (6)*, pp. 1451–1460, (Nov. 15, 1997).

Furnary, A.P., et al., "Multicenter Trial of Dynamic Cardiomyoplasty for Chronic Heart Failure", *Journal of the American College of Cardiology, 28(5)*, pp. 1175–1180, (Nov. 1, 1996).

Gross, M., et al., "Metabolism of D–Ribose Administered Continuously to Healthy Persons and to Patients with Myoadenylate Deaminase Deficiency", *Klin Wochenschr, 67*, pp. 1205–1213, (1989).

Gross, M., et al., "Ribose administration during exercise: effects on substrates and products of energy metabolism in healthy subjects and a patient with myoadenylate deaminase deficiency", *Klin. Wochenshr., 69*, pp. 151–155, (1991).

Jessup, M., "Optimizing Medical Management of the Patient with Severe Heart Failure Awaiting Cardiac Transplanting", *Cardiology—In Review, 4 (5)*, pp. 286–291, (Sep. 1996).

Ma, L., et al., "Nitroglycerin enhances the ability of dobutamine stress echocardiography to detect hibernating myocardium", *Circulation, vol. 96, No. 11*, pp. 3992–4001, (Dec. 2, 1997).

Mahoney, Jr., J.R., et al., "A comparison of different carbohydrates as substrates for the isolated working heart", *Journal of Surgical Research, 47*, pp. 530–534, (1989).

Nagueh, S.F., et al., "Identificqation of Hibernating Myocardium: comparative accuracy of myocardial contrast echocardiography, rest–redistribution thallium–201 tomography and dobutamine echocardiography", *JACC vol. 29, No. 5*, pp. 985–993, (Apr. 1997).

Pliml, W., et al., "Effects of ribose on exercise–induced ischaemia in stable coronary artery disease", *The Lancet, 340*, pp. 507–510, (Aug. 29, 1992).

Sawada, S.G., et al., "Echocardiographic Detection of Coronary Artery Disease During Dobutamine Infusion", *Circulation, 83 (5)*, pp. 1605–1614, (May 1991).

(List continued on next page.)

*Primary Examiner*—James H Reamer
(74) *Attorney, Agent, or Firm*—Schwegman, Lundberg, Woessner & Kluth, P.A.

(57) ABSTRACT

Precursors of adenosine triphosphate are administered orally to increase intracellular ATP concentration as dietary supplements or for treatment of reduced energy availability resulting from strenuous physical activity, illness or trauma. Pentose sugars are administered individually, mixed into dry food or in solution. The preferred pentose is D-ribose, singly or combined with creatine, pyruvate, L-carnitine and/or vasodilating agents. Additionally, magnesium, electrolytes, fatty acids and hexose sugars can be used. The compositions and methods of this invention are especially beneficial to mammals having reduced energy availability or high energy demand.

11 Claims, 3 Drawing Sheets

OTHER PUBLICATIONS

Schultis, K., et al., "Xylitol in metabolism during stress conditions", *Medizin und Ernahrung, 11, Jahrgang*, pp. 59–63, (1970).

St. Cyr, J.A., et al., "Enhanced high energy phosphate recovery with ribose infusion after global myocardial ischemia in a canine model", *Journal of Surgical Research, 46* (2), pp. 157–162, (Feb. 1989).

Tan, Z.T., et al., "Verapamil,ribose andadenine enhance resynthesis of postichemic myocardial ATP", *Life Sciences, 55* (*18*), pp. PL 345–PL 349, (1994).

Tullson, P.C., et al., "Adenine Nucleotide Syntheses in Exercising and Endurance–trained Skeletal Muscle", *The American Journal of Physiology, 261* (*2*), pp. C342–C347, (1991).

Tullson, P.C., et al., "IMP Metabolism in Human Skeletal Muscle After Exhaustive Exercise", *The American Journal of Physiology*, pp. 146–152, (1995).

Wagner, D.R., et al., "Effects of oral ribose on muscle metabolism during bicycle ergometer in AMPD–deficient patients", *Annals of Nutrition and Metabolism, 35* (*5*), pp. 297–302, (1991).

Zimmer, H.G., et al., "Ribose accelerates the repletion of the ATP pool during recovery from reversible ischemia of the rat myocardium", *Journal of Molecular and Cellular Cardiology, 16* (*9*), pp. 863–866, (Sep. 1984).

Zollner, N., et al., "Myoadenylate Deaminase Deficiency: Successful Symptomatic Therapy by High Dose Oral Administration of Ribose", *Klin Wochenschr, 64*, pp. 1281–1290, (1986).

COMPOSITIONS FOR INCREASING ENERGY IN VIVO

This application is a continuation of International Patent Application No. PCT/US99/13720, filed on Jun. 17, 1999, which in turn claims priority to U.S. patent application Ser. No. 09/290,789, filed on Apr. 12, 1999, all of which are incorporated herein by reference.

FIELD OF THE INVENTION

The present invention relates to compositions and methods for increasing the energy available to mammals having reduced energy availability or expending high levels of energy. Such mammals include humans with illnesses resulting in reduced intracellular adenosine triphosphate (ATP), humans engaged in heavy physical activity such as athletes or laborers, and humans desiring to increase their energy levels. Other mammals such as dogs and cats are also included in the present method. Administration of the compositions of the invention provides increased levels of blood and intracellular ATP, extends the time and intensity at which a mammal can exercise, and increases the rate of oxygen utilization by the exercising subject. Non-exercising mammals and those that expend a higher than normal level of energy during recovery from physical insults such as trauma, burns and sepsis also benefit from administration of the compositions of the invention.

BACKGROUND OF THE INVENTION

It is well known that the energy coinage of the cell is adenosine triphosphate (ATP). During anabolism, the energy derived from the metabolism of nutrients is transferred to high energy phosphate bonds of ATP. The energy in these bonds is expended during the energy consumption phase. An important and "costly" expenditure, in which ATP is rapidly cycled, is that required for muscular contraction.

The energy buildup steps occur within the muscle cell during two basic processes. Oxidative phosphorylation replenishes ATP by the breakdown of circulating fatty acids, glucose and intramuscular glycogen and triglycerides. Anaerobic phosphorylation provides ATP from creatine phosphate, circulating glucose and intramuscular glycogen via kinase reactions such as the myokinase reaction.

U.S. Pat. No. 5,714,515 describes the administration of compositions containing pyruvate, an intermediate breakdown product of glucose, to enhance recovery from surgical or accidental trauma, shock, exhaustion due to prolonged physical effort and other indications. U.S. Pat. No. 5,709,971 discloses the administration of other glucose metabolites, namely glyceraldehyde-3-phosphate, phosphoenolpyruvate and 3-phosphoglycerate, in combination with nicotineadeninedinucleotide, coenzyme A and acetyl coenzyme A.

A different approach to increasing the substrates available for production of ATP that has been employed is the administration of the amino acid L-carnitine, which is thought to enhance the transport and absorption of fatty acids into mitochondria, the site of oxidative phosphorylation. U.S. Pat. No. 4,968,719 describes the use of L-carnitine for the treatment of peripheral vascular diseases.

Regardless of whether the high energy phosphate bonds of ATP are generated oxidatively or anaerobically, and irrespective of the substrates used for its generation, ATP cannot be synthesized unless the precursors of the ATP molecule itself are available. The resynthesis of the ATP molecule can occur by de novo or salvage pathways.

In the synthesis of ATP via the nucleotide salvage pathway, the nucleotide precursors that may be present in the tissue are converted to AMP and further phosphorylated to ATP. Adenosine is directly phosphorylated to AMP, while xanthine and inosine are first ribosylated by 5-phosphoribosyl-1-pyrophosphate (PRPP) and then converted to AMP. Ribose is found in the normal diet only in very low amounts, and is synthesized within the body by the pentose phosphate pathway. In the de novo synthetic pathway, ribose is phosphorylated to PRPP, and condensed with adenine to form the intermediate adenosine monophosphate (AMP.) AMP is further phosphorylated via high energy bonds to form adenosine diphosphate (ADP) and ATP.

Synthesis by the de novo pathway is slow. Normally, AMP synthesis is believed to occur mainly by the salvage pathway, however, following anoxia or ischemia, the activity of the de novo pathway is increased.

During energy consumption, ATP loses one high energy bond to form ADP, which can be hydrolyzed to AMP. AMP and its metabolites adenine, hypoxanthine and inosine are freely diffusible from the muscle cell and may not be available for resynthesis to ATP via the salvage pathway.

In U.S. Pat. No. 4,719,201, it is disclosed that when ATP is hydrolyzed to AMP in cardiac muscle during ischemia, the AMP is further metabolized to adenosine, inosine and hypoxanthine, which are lost from the cell upon reperfusion. In the absence of AMP, rephosphorylation to ADP and ATP cannot take place. Since the precursors were washed from the cell, the nucleotide salvage pathway is not available to replenish ATP levels. It is disclosed that when ribose is administered via intravenous perfusion into a heart recovering from ischemia, recovery of ATP levels is enhanced.

Pliml, in German Patent No. 4,228,215, found that oral ribose was effective in treating cardiac insufficiency and hypovolemic shock in humans.

The advantage of the administration of pentoses such as ribose or xylitol to prevent pain and stiffness of skeletal muscle in patients suffering from the autosomal recessive genetic disease myoadenylate deaminase (MAD) deficiency was shown by Zöllner et al. (Klinische Wochenshritt 64:1281–1290, 1986.) This disease is characterized by permanent muscular hypotonia, excessive muscular weakness, fatigue, soreness, burning pain, stiffness and cramps. These symptoms are considered to be consequences of the interruption of the ATP cycle. Dephosphorylation of ATP is inhibited by the accumulation of AMP, resulting in less available energy to effect muscle contraction and relaxation. However, even though symptoms of MAD-deficient patients were relieved by administration of ribose, the intracellular levels of adenine nucleotides remained abnormally high and normal volunteers experienced no beneficial effect from ribose administration. (Gross, Reiter and Zöllner, Klinische Wochenshritt, 67:1205–1213, 1989.)

Tullson et al. (Am. J. Physiol., 261 (Cell Physiol. 30) C343–347, 1991) cite references showing that high intensity exercise increases degradation and subsequent loss of AMP from isolated muscle. They further disclose that adding ribose to the perfusate in a rat hindquarter preparation increases the de novo synthesis of AMP in sedentary muscle, but does not eliminate the decline in de novo synthesis seen in contracting muscle.

Carniglia, et al, U.S. Pat. No. 4,871,718, disclose that when a complex mixture comprising amino acids, metabolites, electrolytes and ribose or a precursor of ribose, was administered orally as a dietary supplement to race horses, increases in intracellular ATP levels and physical performance result. The performance evaluation was anecdotal, however, based on the subject's performance history.

Thus, a continuing need exists for simple methods to enhance skeletal muscle performance in normal mammals; that is, mammals that are not at the time of application of the method experiencing ischemia, prior to or undergoing physical activity. A need also exists for a method to increase the energy level of mammals to provide an increased feeling of well-being.

SUMMARY OF THE INVENTION

The present invention provides compositions and methods of increasing the energy level in a mammal. It is believed that the present compositions and methods function by stimulating the synthesis of ATP in a mammal experiencing a less than optimal availability of ATP in order to support cellular function. Specifically, a pentose such as D-ribose is given orally before, during and after a period of high ATP demand, in amounts effective to enhance the energy of the mammal. Mammals given ribose are able to exercise longer, to achieve a higher intensity and subjectively have more energy than those not given ribose.

It is proposed that the cellular concentration of PRPP is the limiting factor in recovery or increase of ATP levels via either the de novo or nucleotide salvage pathways and that the administration of ribose can stimulate ATP synthesis, providing larger pools of ATP for energy expenditure. Mammals experiencing a less than optimal availability of ATP include normal, healthy subjects undergoing high energy demand such as athletes, and workers performing heavy labor. It is further proposed that normal subjects even in the resting state will experience a positive feeling of enhanced well-being after administration of effective amounts of ribose.

The availability of PRPP appears to control the activity of both the salvage and de novo pathways, as well as the direct conversion of adenine to ATP. Production of PRPP from glucose appears to be limited by the enzyme glucose-6-phosphate dehydrogenase (G6PDH). Glucose is converted by enzymes such as G6PDH to ribose-5-phosphate and further phosphorylated to PRPP, which augments the de novo and salvage pathways, as well as the utilization of adenine. The addition of ribose bypasses this rate limiting enzymatic step.

Also included in the group of subjects benefiting from the method of the invention are mammals having a chronic low energy level due to advanced age, trauma, sepsis, or such disease conditions as congestive heart failure and other chronic illnesses.

Compositions that enhance the pentose benefit are also provided. Such compositions preferably comprise at least one of magnesium,-creatine, pyruvate, L-carnitine, pentose, other energy metabolites and optionally at least one vasodilating substance. Of these, creatine and magnesium are preferred for combination with ribose. Mammals undergoing high energy demand and loss of fluids also benefit from a composition that further comprises electrolytes and an additional energy source such as carbohydrate.

DETAILED DESCRIPTION OF THE INVENTION

Figure 1:
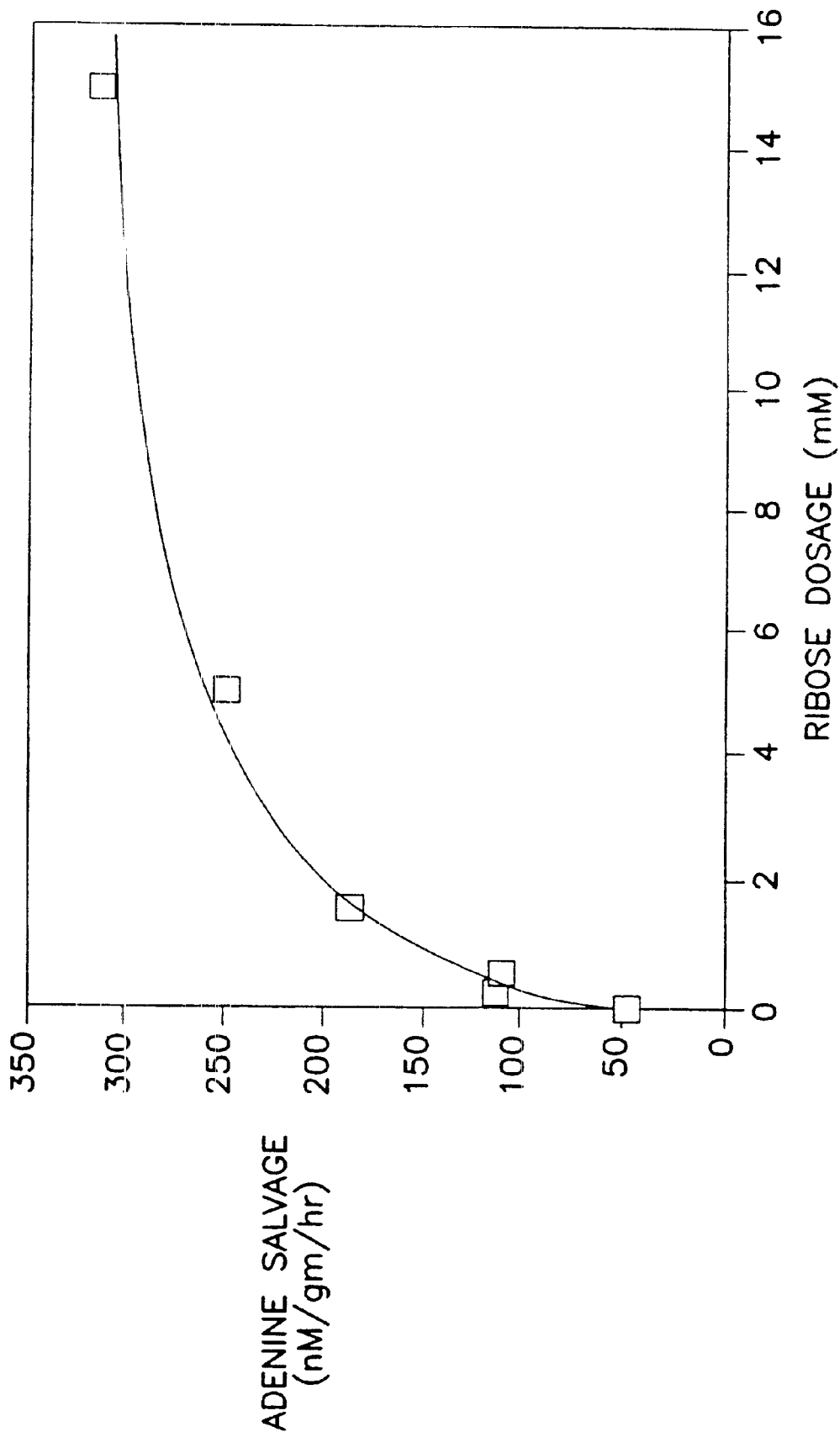
FIG. 1 shows the dose response of the adenine salvage pathway in normal adult rats to the administration of ribose.

The present invention provides a method of stimulating the synthesis of ATP by the oral administration of a pentose and provides pentose-containing compositions that are especially beneficial to mammals undergoing high energy demands or those having chronic low energy levels.

For the purpose of describing this invention, the following terms have the following meanings:

1. "Pentose" means a monosaccharide, including but not limited to, ribose, D-ribose, ribulose, xylitol, xylulose, and any 5-carbon precursor of ribose.
2. "Vasodilator" includes any substance that causes dilation of blood vessels, including adenine, hydralazine, arginine and nitroglycerine administered transdermally or orally.
3. "Intracellular ATP levels" means ATP concentrations measured directly by tissue biopsy or nuclear magnetic resonance or indirectly by blood ATP concentration.
4. "Other energy metabolites and co-factors" means creatine, co-enzymes, intermediates of the tricarboxylic acid, pentose phosphate or glycolytic enzyme pathways, pyrimidine and purine nucleotides and minerals.

The compositions preferably contain an energy-enhancing amount of pentose dissolved or dispersed in an aqueous vehicle such as water, that may optionally contain minor but effective amounts of additives such as polyols, preservatives, flavorings, colorings and the like. Compositions containing pentoses adapted for oral administration also include solid dosage forms such as tablets, lozenges, capsules and the like. Pentoses may also be incorporated in solid nutriments such as bars, moist or dry dog food, powders or drink mixes. Effective total dosages of ribose, which can be extrapolated to other pentoses, are disclosed hereinbelow.

Because pentoses are naturally occurring sugars with a pleasant taste and virtually no toxicity, subjects may be encouraged to self-administer pentose in the form of tablets, lozenges, powders, suspensions, solutions, or mixed in with solid food. When the subject is canine or feline, pentose can be easily integrated into "senior diet" or "cardiac diet" and separate administration is not necessary. When the subject is human, pentose can be included in drinks, bars, shakes or snack food. The preferred pentose is ribose or xylitol. The preferred dosage is 0.1 to 100 gm pentose per day, preferably 1 to 20 gm pentose per day. An average adult human may find that 4 to 8 gm pentose per day is sufficient to provide the benefits of the invention. The upper dose is limited only by the taste preference of the subject, although at very high doses, subjects may experience diarrhea. The dose may be given once a day in a single unit dosage form, but preferably is given two or three times throughout the day, most conveniently during or following mealtime.

During strenuous activity, individuals may sweat profusely, requiring replacement of body fluids and electrolytes. Subjects such as dogs, which do not sweat, lose copious amount of water through the lungs and also require fluid replacement. In addition to the advantages provided by pentoses alone, with carnitine and or vasodilating agents, it is convenient to include other components within a replacement solution to be drunk during and following exercise.

Rehydration solutions such as Gatorade® Thirst Quencher, and Max® drinks are among those popular with athletes.

These sustained energy and anabolic formulas are generally made up of different carbohydrates, including corn syrup, sucrose, fructose, and maltodextrin; proteins, including casein and other proteins from milk and soybean; and lipids, including corn, soy, safflower, and canola oils and medium chain triglycerides. Efforts at improving such "performance drinks" continue.

U.S. Pat. No. 5,292,538 describes an energy sustaining composition containing fructose, glucose, hydrolyzed protein and magnesium liganded to an amino acid chelate. Other ingredients noted as especially advantageous include potassium, phosphorus, manganese, zinc, boron, copper, molybdenum, chromium, vanadium, vitamins $B_{1,2,5,6 \text{ and } 12}$, C, E and carnitine.

U.S. Pat. No. 5,114,723 describes hypotonic beverage compositions for oral administration comprising electrolytes, minerals, carbohydrates and other ingredients. The compositions are adjusted to have an osmolarity between 100 and 270 mOs/l.

Each of these rehydration drinks will be improved by the addition of from about 1 to 20% pentose, most preferably 10% by weight to volume. The amount of pentose to be added will depend on the composition of other nutrients, to keep the osmolarity within the preferred limits. These drinks will be further improved by the addition of other energy metabolites and co-factors.

The invention will be further described by reference to the following examples.

EXAMPLE 1

Effect of D-ribose on Nucleotide Salvage in Resting Rat Muscle

It has been theorized but not objectively shown that ribose, via PRPP synthesis, increases the rate of ATP synthesis via the nucleotide salvage pathway. However, nothing is known about the total adenine nucleotide (TAN) or ribose levels in the resting muscle and therefore, it is possible that the synthetic enzyme pathway is already saturated and that administration of ribose does not increase ATP levels in normal, non-ischemic skeletal muscle. In order to demonstrate the effect of ribose on the pathway, plantaris complex muscles of healthy adult male Sprague-Dawley rats were surgically exposed and perfused with reconstituted blood perfusion medium containing amino acids, mM glucose and 100 μU of bovine insulin/ml. The muscle was perfused with reconstituted blood medium at ~40 ml/min, providing tissue perfusion of approximately 0.65 ml/min. Varying concentrations of D-ribose were added to the perfusate to bring the concentration to 0.156 mM, 0.5 mM, 1.58 mM, 5.0 mM and 15.0 mM. The muscle was perfused for 30 minutes. A minimum of two rats was used for analysis at each dose of ribose tested.

Following perfusion, muscle sections were quickly dissected from the limb and freeze-clamped with aluminum tongs chilled in liquid nitrogen. Muscle sections were lyophilized and reconstituted in distilled water for subsequent-separation of adenine nucleotides by reverse-phase high pressure liquid chromatography. Results are expressed as salvage of adenine (i.e., formation of ATP) in nanomoles salvaged per gram wet weight of muscle per hour (nM/gm/hr).

TABLE I

Ribose Skeletal Muscle Dose-Response Kinetics

| mM Ribose | Observed | Saturation Kinetics with Base |
|---|---|---|
| 0.000 | 48.6 | |
| 0.158 | 113.0 | 85.82 |
| 0.500 | 110.0 | 118.68 |
| 1.000 | | 154.12 |
| 1.580 | 188.5 | 183.51 |
| 2.000 | | 199.74 |
| 2.500 | | 215.29 |
| 3.000 | | 227.85 |
| 5.000 | 250.0 | 260.68 |
| 15.000 | 315.5 | 310.37 |

As is shown in FIG. 1 and Table I, adenine salvage at zero millimolar (mM) ribose is less than 50 nM/gm/hr and doubles with administration of 0.158 mM ribose. At 5 mM ribose, the rate of ATP synthesis reaches 250 nM/gm/hr. These results show that normal, healthy muscle has low baseline levels of ribose and nucleotide salvage capability, which can be increased by the administration of ribose.

EXAMPLE 2

Increased Exercise Capacity in Normal Subjects

Four healthy, fit subjects in the age range 24 to 26 years of age were tested. The group was selected to be homogeneous regarding fitness level, gender and mean age with no known metabolic, neuronal, endocrine or cardiopulmonary disorders. All were capable of or had experience with cycling. The study protocol included four phases: (1) an initial baseline phase consisting of no exercise session; (2) a loading phase including three days of administration of either D-ribose or placebo (glucose) three times per day; (3) a training phase of three days employing exercise sessions characterized by serial (N=6) bouts of short (10 second) high-intensity cycle sprints at 7% body mass resistance with 50 second rest periods between sprints twice per day (morning and afternoon), and (4) a recovery phase for a period of 48 hours after the final training session. FIG. 1 is a diagram of a single cycle sprint bout.

Muscle biopsies (MB) were performed on the vastis lateralis muscle using both legs in order to evenly distribute and minimize sampling and possible muscle soreness per leg due to the biopsy itself. The first MB was collected at rest at the beginning of the study to establish a baseline and immediately after the first training-session of day 0 or the first phase. During the loading phase, no MB was taken. Muscle Biposies were taken following the final training session and after 48 hours of recovery.

Two subjects were randomly selected for inclusion into the placebo or ribose group. Ribose or glucose was administered orally in a 250 ml iso-osmotic solution containing 10.0 grams of either ribose or placebo three times per day for three days preceding training (loading phase) and for three days during training (training phase). One-half liter isotonic electrolyte solution was given immediately post exercise and again 30 minutes later to avoid dehydration.

The concentration of the following analytes was determined in the MB samples: ATP, ADP, AMP, IMP (inosine monophosphate), TAN (total adenine nucleotides), creatine phosphate and creatine.

TABLE II

Ribose Athlete Study
Mean Power Per Kilogram (Watts)

| Subject | 1 | 2 | 3 | 4 | 5 | 6 | Average | |
|---|---|---|---|---|---|---|---|---|
| 1P | 6.0 | 6.7 | 7.3 | 7.4 | 7.3 | 7.5 | 7.0 | |
| 2R | 6.9 | 7.5 | 7.8 | 7.6 | 7.9 | 7.4 | 7.5 | |
| 3R | 8.7 | 9.2 | 9.1 | 9.0 | 8.5 | 8.2 | 8.8 | |
| 4P | 7.5 | 8.0 | 7.7 | 8.7 | 8.0 | 7.6 | 7.9 | |
| Placebo | 6.8 | 7.4 | 7.5 | 8.0 | 7.6 | 7.5 | 7.5 | 100.0% |
| Ribose | 7.8 | 8.4 | 8.5 | 8.3 | 8.2 | 7.8 | 8.2 | 109.0% |

TABLE III

Ribose Athlete Study
Peak Power Per Kilogram (Watts)

| Subject | 1 | 2 | 3 | 4 | 5 | 6 | Average | |
|---|---|---|---|---|---|---|---|---|
| 1P | 6.8 | 7.9 | 8.6 | 8.6 | 8.3 | 9.0 | 8.2 | |
| 2R | 7.9 | 8.8 | 9.2 | 9.0 | 9.4 | 8.7 | 8.8 | |
| 3R | 9.8 | 10.6 | 10.7 | 10.7 | 10.1 | 9.9 | 10.3 | |
| 4P | 7.7 | 8.6 | 8.7 | 9.4 | 8.8 | 9.0 | 8.7 | |
| Placebo | 7.7 | 8.6 | 8.7 | 9.4 | 8.8 | 9.0 | 8.7 | 100.0% |
| Ribose | 8.9 | 9.7 | 10.0 | 9.9 | 9.8 | 9.3 | 9.6 | 109.9% |

TABLE IV

Ribose Athlete Study
Total Power Per Kilogram

| Subject | 1 | 2 | 3 | 4 | 5 | 6 | Average | |
|---|---|---|---|---|---|---|---|---|
| 1P | 59.1 | 67.0 | 72.7 | 73.3 | 72.5 | 74.2 | 69.8 | |
| 2R | 71.9 | 74.7 | 77.1 | 75.6 | 78.1 | 73.4 | 75.1 | |
| 3R | 86.8 | 91.9 | 91.3 | 90.0 | 85.4 | 82.5 | 88.0 | |
| 4P | 74.5 | 80.3 | 76.8 | 87.4 | 80.0 | 76.4 | 79.2 | |
| Placebo | 66.8 | 73.6 | 74.8 | 80.4 | 76.3 | 75.3 | 74.5 | 100.0% |
| Ribose | 79.3 | 83.3 | 84.2 | 82.8 | 81.8 | 77.9 | 81.6 | 109.5% |

Figure 2:
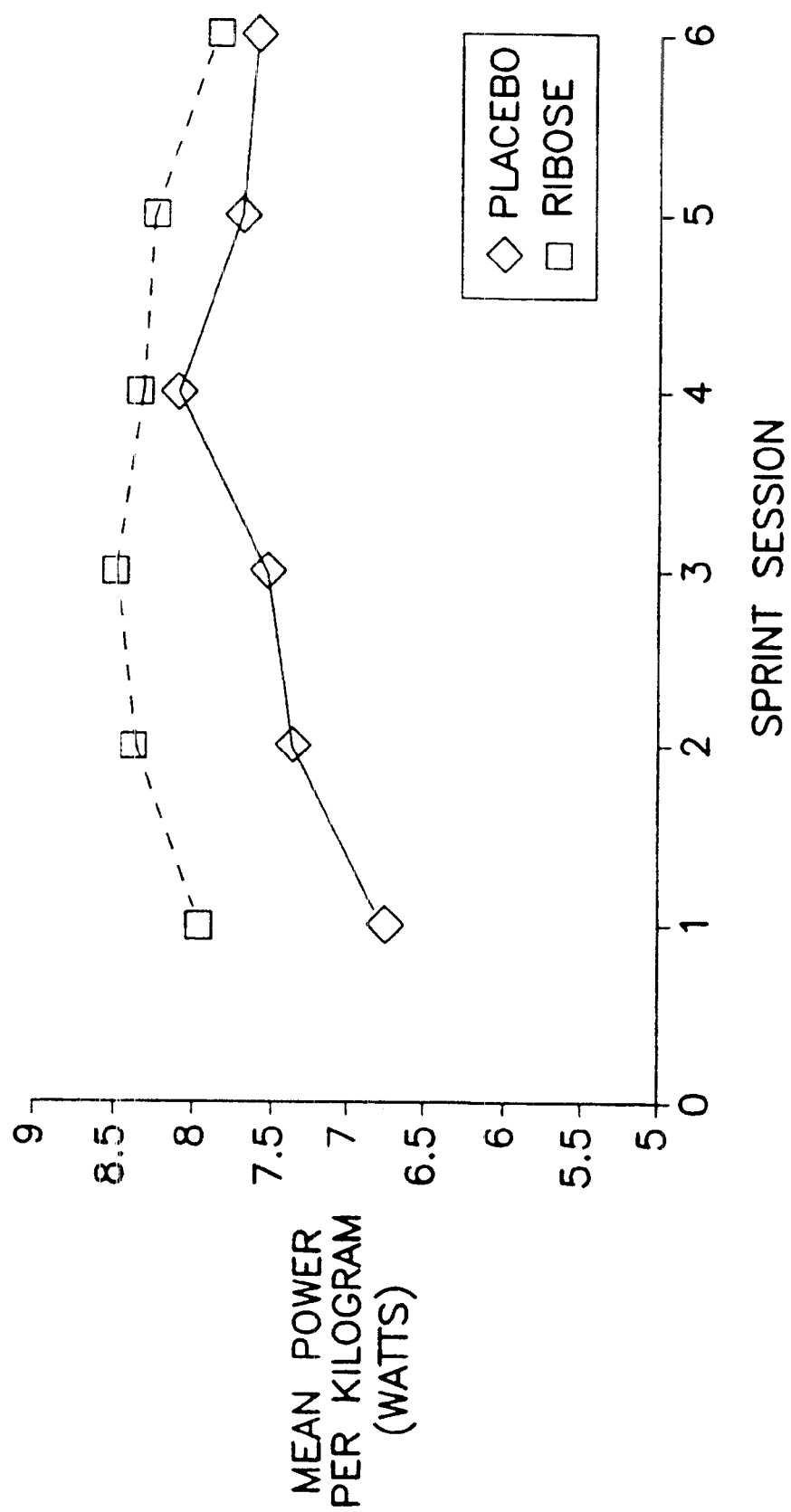
FIG. 2 shows the mean power output per sprint session of normal adult humans, following administration of ribose or placebo, as measured on an exercycle.
Figure 3:
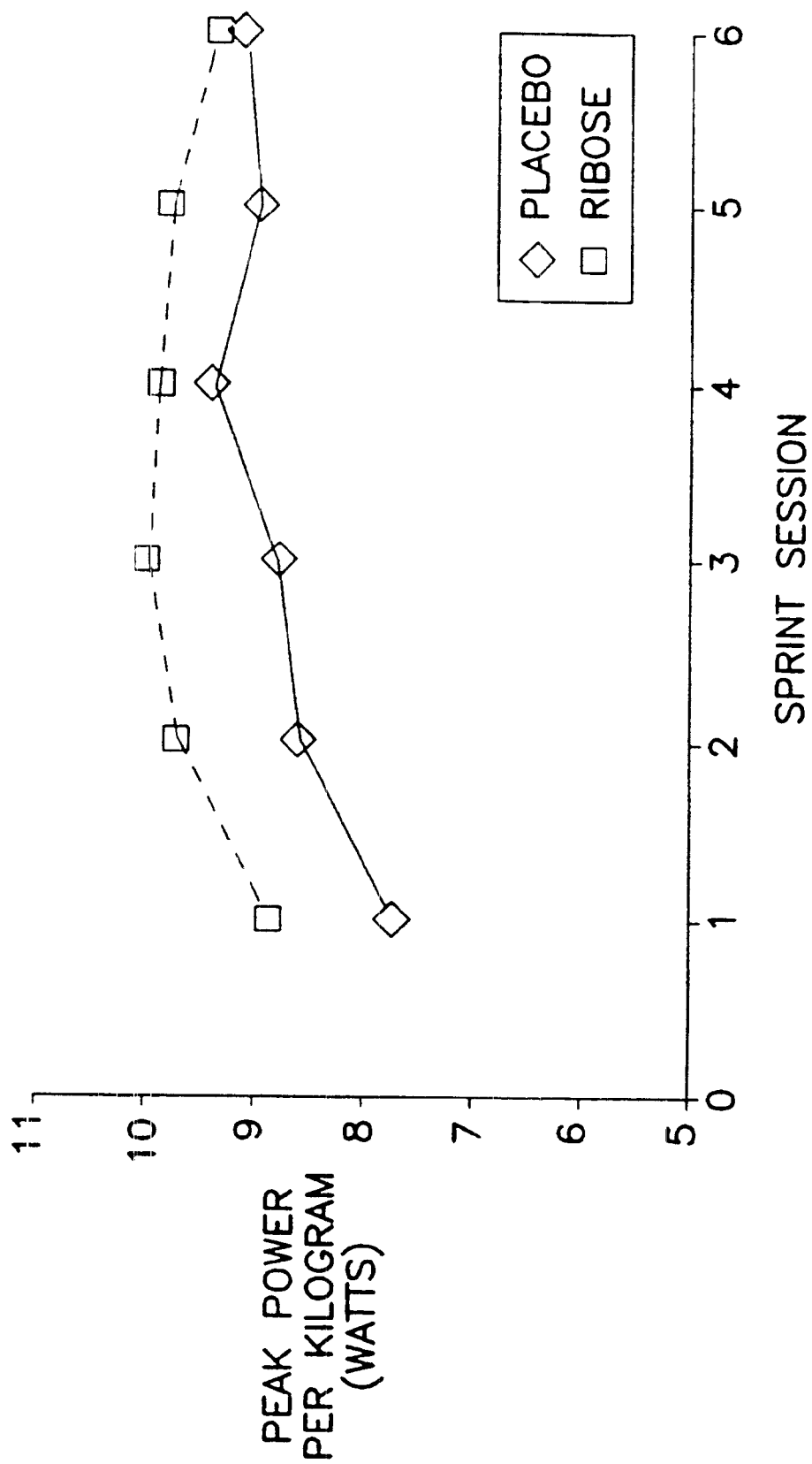
FIG. 3 shows the peak power output per sprint session of normal adult humans, following administration of ribose or placebo, as measured on an exercycle.

As can be seen from Tables II to IV and FIGS. 2 and 3, administration of ribose increased performance by 9%.

The improvement in performance is reflected in the ATP levels in the muscle biopsies. As shown in Table V, the subjects preloading with ribose for three days began the training phase with higher levels of ATP, which declined significantly more than that of the placebo group after the sprint bouts, indicating that ATP was being utilized more efficiently. Recovery of the ribose group at 48 hours was 82% of the initial level, compared to 78% in the placebo group.

TABLE V

Mean ATP Values (mmol/kg dw)

| Group | Pre | Post | Recovery | Recovery % of Pre | Change Pre-Post | Change Post-Rec |
|---|---|---|---|---|---|---|
| Placebo | 23.60 | 20.05 | 18.30 | 78% | −3.55 | −1.75 |
| Ribose | 25.33 | 13.90 | 20.80 | 82% | −11.43 | 6.90 |

EXAMPLE 3
Increased Stamina and Feeling of Well-being in Normal, Untrained Subjects D-ribose, given immediately before and during exercise, can provide a benefit to those subjects who have not been previously trained. Four healthy, normal male volunteers will be tested for sprint power output on an exercycle, as for Example 2 above. Each subject will serve as his own control. Between the sprint bouts, the subjects will cycle slowly and continuously. Total test time will be one hour, with four sprint bouts during the test. Following the initial baseline test and following each sprint bout, the subjects will be given 5 grams of D-ribose in 200 ml. of water or a similar tasting placebo (glucose). Sprint power output will be tested 15 minutes after each ingesting of the test solutions. Each subject will undergo two sessions, one week apart, one with ribose and one with placebo, in randomized order. The placebo will be sweetened with glucose in order to be indistinguishable from the ribose solution. It is expected that the subjects will show higher power output after ribose administration following sustained mild exercise than they showed after placebo administration. It is further expected that the subjects will have a subjectively higher feeling of well being.

EXAMPLE 4
Relief of Exercise Induced Angina

A sixty-eight year old male patient with a history of coronary artery disease, status post triple coronary artery bypass, experienced exercise induced angina. His present medications are: enalapril (an angiotensin converting enzyme inhibitor), carvedilol (a β blocking agent), nitroglycerine patch and nitroglycerine tablets sublingual as needed. The most recent coronary angiogram revealed advancement of his coronary artery disease with total occlusion of one of the bypass grafts. The patient performed poorly on two stress tests. His exercise regimen consisted of a daily walk.

Due to the development of angina, the patient was able to walk less than one mile per day, at which point he took sublingual nitroglycerine. The patient was given oral D-ribose dissolved in about 250 cc. of water. Over a six-month period, the patient received intermittent doses of 5–10 grams per day of D-ribose. Post ribose administration, the patient was able to increase his exercise tolerance to two miles per day without any supplementation of oral nitroglycerine. When the ribose was discontinued, his pre-ribose, anginal-inducing exercise state recurred, which necessitated the use of supplemental oral nitroglycerine. Resumption of oral ribose allowed the patient to walk two miles per day, without angina or the need for nitroglycerine. His subjective evaluation of the ribose treatment is there is "much less angina pain. I feel better, have more energy and can be more active without pain or pills [nitrogycerine]."

EXAMPLE 5
Improved Treadmill Test Performance

A sixty-year old male patient with stable coronary artery disease was observed to show a greater than fifty percent occlusion of more than one epicardial coronary artery and stable angina. The patient was tested for treadmill performance. After two baseline treadmill tests, following the Bruce protocol, he received orally administered D-ribose (40 gm in three divided doses daily) for three days and completed a third treadmill test. At each time, the test was to be stopped when a) the patient exhibited ST segment depression of 1 mm or more in the ECG tracing; b) when the patient complained of angina or c) when the patient stopped due to dyspnea or fatigue. In each test, this patient concluded the test due to shortness of breath, but experienced no angina.

As can be seen from Table VI, the administration of D-ribose for three days before the final treadmill test increased energy and heart function as measured by decrease in rate-pressure product at each stage of testing, including rest (zero time). It is generally accepted that the product of heart rate and systemic pressure is a measure of myocardial function and energy level, with lower numbers indicating better myocardial function. As a result of the administration of ribose, average tolerated time on the treadmill increased. In addition to the objective measure of efficacy, the patient subjectively reported feeling more energetic during ribose administration.

TABLE VI

Rate-pressure product as beats per minute times systolic blood pressure mm Hg

| Time | Baseline 1 | Baseline 2 | Average | Test | % change |
|---|---|---|---|---|---|
| 0 (rest) | 11,088 | 9,272 | 10,180 | 9,177 | −9.55% |
| 3 minutes | 17,574 | 13,468 | 15,521 | 15,272 | −1.60% |
| 6 minutes | 26,500 | 22,344 | 24,422 | 20,592 | −15.68% |
| 9 minutes | 33,396 | 29,526 | 31,461 | 25,356 | −9.87% |
| Tolerated time, sec. | 483.00 | 545.00 | 514.00 | 540.00 | 5.06% |

In the Bruce protocol, the treadmill speed in increased in three minute increments from 1.7 to 6.0 miles per hour, while the slope is increased from 10 to 22%.

EXAMPLE 6
Self Administration of Ribose

Patients with chronic illnesses, including but not limited to coronary artery disease, AIDS, intermittent claudication, tuberculosis and chronic fatigue syndrome, that are characterized by low energy levels, and even those subjects free of overt disease but having low energy due to advanced age, trauma, burns, and recovery from illness or surgery, are benefitted by being able to raise their energy levels without continual medical intervention. Many individuals with relatively stable disease live a day to day existence by conforming to an altered life style, coupled with pharmaceutical supplementation. Often, such subjects are inhibited from undertaking a regimen of moderate physical activity from fear of inducing unpleasant effects, such as angina, breathlessness, muscle soreness, cramping or a feeling of exhaustion. Such avoidance lowers the quality of life of the subject and engenders an ever-present background anxiety. In addition, the benefits of moderate exercise, which include improved digestion, sleep and a more relaxed and positive state of mind, are denied to such subjects. Even subjects free of disease and considered healthy may be dissatisfied with their subjective feeling of energy level and well being.

An example of a subject having no overt disease who benefitted from self-administered ribose is a fifty-five year old male. He had adhered to a strict weekly exercise regimen most of his life until sustaining a systemic bacterial infection, which required admission to the intensive care unit for one month and rehabilitation for an additional month. His cardiovascular and pulmonary systems were predominantly affected during and following his illness and function had not recovered to its previous levels, or to his satisfaction, after one year.

Following convalescence, he has attempted to resume an exercise regimen, which involves running on a treadmill four days a week and lifting weights for two days a week. The runs were restricted to short intervals. Following the daily exercises, he has continuously experienced fatigue to the point of exhaustion and has required frequent naps. The patient began self-administering oral D-ribose at two doses per day, 4–5 grams per dose. Within seven days, he testified that his "pep" and exercise tolerance increased. For the first time since his illness, he is able to run as long as 30 minutes on the treadmill. He still experiences a Degree of fatigue, but has been able to discontinue the naps after exercise. He continues on the daily oral doses of ribose, along with his scheduled exercises and feels a continuing improvement in his energy level after four weeks of ribose administration. He has experienced no adverse effects from the ribose.

EXAMPLE 7
Effect of Ribose with Arginine and/or Carnitine on Subjects with Chronic Conditions As shown in Example 6, subjects experiencing low energy levels are predicted to benefit by the self-administration of pentoses. It is further predicted that ingestion of a orally acceptable vasodilator such as L-arginine will have an additional beneficial effect on such subjects. It is still further predicted that ingestion of L-carnitine to transport fatty acids into the mitochondria will provide an additional beneficial effect to such subjects. It is still further predicted that the addition of other energy metabolites and co-factors will provide additional beneficial effects to such subjects.

Arginine is known to be a precursor of the endothelium-relaxing factor nitric oxide. In vitro analyses have determined that under normal circumstances, an excess of L-arginine is available to endothelial cells. However, in vitro studies have also shown that endothelium-dependent vasodilatation is improved with the addition of L-arginine, when L-arginine stores are depleted or if L-glutamine, an antagonist of L-arginine, is present. It was not known, prior to this invention, if oral arginine can enhance cardiac perfusion and thus the distribution of ribose to muscle tissue. The test group chosen will be human patients with low energy levels due to cardiac disease, which is an available and well-studied group. The results are expected to apply equally to other subjects having low energy levels, such as subjects with debilitating diseases and elderly human and canines.

Thirty adult (45–70 years of age) subjects with known stable coronary artery disease, but without resting ischemia, will be randomized into three separate groups. Each patient will be subjected to a serial exercise treadmill testing to initially qualify for admission into this protocol. A final treadmill test will be performed after a three day course of either L-arginine, D-ribose, L-carnitine or a combination of L-arginine, D-ribose and L-carnitine. The end points of this study will investigate-time to development of angina pectoris and/or electrocardiographic changes during treadmill exercise.

It is expected that these test subjects will show even more improvement than the 10% decrease in rate-pressure and 5% increase in tolerated time as shown in Example 2.

All publications and patents cited herein are incorporated by reference as though fully set forth. This invention has been described with respect to various specific and preferred embodiments. However, it should be understood that many variations or modifications may be made while remaining within the spirit and scope of the invention.

We claim:
1. A method for raising the skeletal muscle ATP levels of a healthy mammal which comprises the oral administration of an effective amount of a pentose to said mammal.
2. The method according to claim 1 wherein the pentose is ribose.
3. The method according to claim 1 wherein the mammal has increased energy demand.
4. The method according to claim 1 wherein the mammal is exercising strenuously.
5. A composition to be administered for raising the skeletal muscle ATP levels in mammals which comprises an effective amount of a pentose.

6. A composition according to claim 5 wherein the pentose is ribose.

7. A method for raising the energy level in a racehorse which comprises the administration of an effective amount of a pentose.

8. The method of claim 7 wherein the pentose is ribose and the effective amount is 30 to 100 grams of ribose.

9. The method of claim 7 wherein the pentose is administered at least two times daily.

10. A method of administering ribose to a racehorse comprising spreading 30 to 100 grams of dry ribose on top of the racehorse's feed.

11. A method of administering ribose to a racehorse comprising dissolving 30 to 100 grams of ribose in about 100 ml of water to form a solution and placing the solution in the racehorse's mouth.

\* \* \* \* \*